US005541075A

United States Patent [19]
Wisnewski et al.

[11] Patent Number: 5,541,075
[45] Date of Patent: Jul. 30, 1996

[54] CARBOHYDRATE-BASED VACCINE AND DIAGNOSTIC REAGENT FOR TRICHINOSIS

[75] Inventors: Nancy Wisnewski; Robert B. Grieve; Donald L. Wassom; Michael R. McNeil, all of Fort Collins, Colo.

[73] Assignee: Heska Corporation, Fort Collins, Colo.

[21] Appl. No.: 14,449

[22] Filed: Feb. 5, 1993

[51] Int. Cl.$^6$ .......................... G01N 33/569; A61K 31/70
[52] U.S. Cl. .................. 435/7.22; 435/7.1; 514/25; 514/53; 514/54; 514/61; 424/265.1
[58] Field of Search .................... 424/88, 265.1, 424/258.1, 815; 514/25, 54, 61, 53; 435/7.1, 7.22

[56] References Cited

U.S. PATENT DOCUMENTS

| | | | |
|---|---|---|---|
| 3,892,529 | 7/1975 | Giles | 435/267 |
| 3,918,818 | 11/1975 | Giles | 356/239 |
| 4,670,384 | 6/1987 | Gamble et al. | 435/7.22 |
| 4,795,633 | 1/1989 | Murrell et al. | 424/265.1 |
| 4,833,168 | 5/1989 | Wyvratt, Jr. | 514/450 |
| 5,008,250 | 4/1991 | Fisher et al. | 514/30 |
| 5,073,567 | 12/1991 | Kojima et al. | 514/450 |
| 5,143,712 | 9/1992 | Brandley et al. | 424/1.73 |

FOREIGN PATENT DOCUMENTS

| | | |
|---|---|---|
| 1580539 | 12/1980 | United Kingdom . |
| WO89/00163 | 1/1989 | WIPO . |

OTHER PUBLICATIONS

Carlsson et al, Acta Path. Microbiol Scand Section C, 86:237–244, 1978.
Roitt et al *Immunology* 3rd ed, Mosby, St. Louis 1993 pg. 7.5.
Takata et al, J. Leukoe Biol 41(3):248–256, 1987.
Jennings, H. J. Infect. Dis 165 Suppl 1 pp. 5156–5159, 1992.
Lehninger A. L., *Principles of Biochemistry* Worth Publishers, NY, 1982 p. 278.
Parkhouse et al, Parisitology 99:55–519, 1989.
Dick et al, "Glycocongugates of Bacterial Carbohydrate Antigens" in *Conjugate Vaccines* Cause et al eds, Basel, Contrib Microbiol Immunol vol. 10:48–114, 1989.
Stedmen's Medical Dictionary, William & Wilkins, London 24th Ed 1982 p. 980.
Appleton et al., "Consensus on *Trichinella spiralis* Antigens and Antibodies", pp. 190–192, 1991, *Paras. Today*, vol. 7.
Callahan et al., "*Dirofilaria immitis* Superoxide Dismutase: Purification and Characterization", pp. 245–252, 1991, *Mol. Biochem. Parasitol.*, vol. 49.
Carpenter, "Enzyme–Linked Immunoassays", pp. 2–9, 1992, *The Manual of Clinical Laboratory Immunology, 4th Edition*, Rose et al., eds, Am. Soc. of Microbiol., Washington, D.C.
Chaplin, "A Rapid and Sensitive Method for the Analysis of Carbohydrate Components in Glycoproteins Using Gas–Liquid Chromatography", pp. 336–341, 1982, *Anal. Biochem.*, vol. 123.

Cygler, et al., "Recognition of a Cell–Surface Oligosaccharide of Pathogenic *Salmonella* by an Antibody Fab Fragment", pp. 442–445, 1991, Science, vol. 253, Jul.
Denkers et al., "Trichinella spiralis: Influence of an Immunodominant, Carbohydrate–Associated Determinant on the Host Antibody Response Repertoire", pp. 403–410, 1991, *Exp. Parasitol.*, vol. 72.
Denkers et al., "The Mouse Antibody Response to *Trichinella spiralis* Defines a Single, Immunodominant Epitope Shared by Multiple Antigens", pp. 3152–3159, 1990, *Journ. Immunology*, vol. 144.
Denkers et al., "Characterization of *Trichinella spiralis* Antigens Sharing an Immunodominant, Carbohydrate–Associated Determinant Distinct from Phosphorylcholine", pp. 241–250, 1990, *Mol. Biochem. Parasitol.*, vol. 41.
Fairbairn, "The Biochemistry of *Ascaris*", pp. 491–554, 1957, *Exp. Parasitol.*, vol. 6.
Fairbairn and Passey, "The Lipid Components in the Vitelline Membrane of *Ascaris Lumbricoides* Eggs", pp. 130–134, 1954, *Canadian Journ. of Biochem. and Physiology*, vol. 33.
Gamble et al., "Inoculation of Pigs Against *Trichinella spiralis*, Using Larval Excretory–Secretory Antigen", pp. 2396–2399, 1986, *Am. J. Vet. Res.*, vol. 47, No. 11, Nov.
Gamble, "*Trichinella spiralis*: Immunization of Mice Using Monoclonal Antibody Affinity–Isolated Antigens", pp. 398–404, 1985, *Experimental Parasitol.*, vol. 59.
Gamble et. al., "Comparison of Monoclonal Antibody–Based Competitive and Indirect Enzyme–Linked Immunosorbent Assays for the Diagnosis of Swine Trichinosis", pp. 379–389, 1984, *Vet. Immunology and Immunopathology*, vol. 6.
Gamble et. al., "Diagnosis of Swine Trichinosis by Enzyme–Linked Immunosorbent Assay (Elisa) Using an Excretory–Secretory Antigen", pp. 349–361, 1983, *Vet. Parasitol.*, vol. 13.

(List continued on next page.)

Primary Examiner—James C. Housel
Assistant Examiner—Julie Krsek-Staples
Attorney, Agent, or Firm—Sheridan Ross & McIntosh

[57] ABSTRACT

The present invention relates to Trichinella vaccines that include at least one tyvelose-containing oligosaccharide or functional equivalent thereof, to Trichinella vaccines that include at least one fucose-containing oligosaccharide or functional equivalent thereof, and to the use of such vaccines to protect animals from Trichinella infections, and particularly from trichinosis caused by *Trichinella spiralis* infection. Such vaccines can also be used to produce antibodies that are capable of protecting an animal from Trichinella infections and of diagnosing such infections. The present invention also relates to Trichinella diagnostic reagents that include at least one tyvelose-containing oligosaccharide, or functional equivalent thereof, and use of such reagents to detect Trichinella, and particularly *Trichinella spiralis* infections. The present invention also includes diagnostic kits based on such reagents and anti-*Trichinella-spiralis* drugs based on the knowledge that tyvelose is produced by *Trichinella spiralis* parasites.

5 Claims, No Drawings

OTHER PUBLICATIONS

Gamble et. al., "Monoclonal Antibody–Purified Antigen for the Immunodiagnosis of Trichinosis", pp. 67–74, 1984, *Am. J. Vet. Res.*, vol. 45, Jan.

Gold et. al., "Partial Characterization of two Antigens Secreted by $L_1$ Larvae of *Trichinella spiralis*", pp. 187–196, 1990, *Molecular and Biochem. Parasitol.*, vol. 41.

Hakomori, "A Rapid Permethylation of Glycolipid, and Polysaccharide Catalyzed by Methylsufinyl Carbanion in Dimethyl Sulfoxide", pp. 205–208, 1964, *The Journ. of Biochem.*, vol. 55.

Herrington et. al., "Safety and Immunogenicity in Man of a Synthetic Peptide Malaria Vaccine Against *Plasmodium falciparum* Sporozoites", pp. 257–259, 1987, *Nature*, vol. 328, Jul.

Hey et. al., "Biosynthesis of Tyvelos", pp. 5473–5478, 1966, *The Journ. of Bio. Chem.*, vol. 241, Nov.

Iversen et al., "Antigenic Determinants of *Salmonella* Serogroups A and $D_1$ Synthesis of Trisaccharide Glycosides for Use as Artificial Antigens", pp. 29–40, 1982, *Carbohydrate Research*, vol. 103.

Jezyk et. al., "Ascarosides and Ascaroside Esters in *Ascaris lumbricoides* (Nematoda)", pp. 691–705, 1967 *Comp. Biochem. Physiol.*, vol. 23.

Jezyk et. al., "Metabolism of Ascarosides in the Ovaries of *Ascaris lumbricoides* (Nemotoda)", pp. 707–719, 1967, *Comp. Biochem. Physiol.*, vol. 23.

Jörbeck, et al., "Immunochemistry of *Salmonella* O–Antigens", pp. 11–19, 1979, *Int. Archs Allergy appl. Immun.*, vol. 58.

Jörbeck, et al., "Artificial *Salmonella* Vaccines: *Salmonella typhimurium* O–Antigen–Specific Oligo saccharide–Protein Conjugates Elicit Opsonizing Antibodies that Enhance Phagocytosis", pp. 497–502, 1981, *Infection and Immunity*, vol. 32, No. 2, May.

Kabat, "Antibody (and Lectin) Combining Sites for Elucidating Structures; Inhibition Reactions for Elucidating Structures", pp. 176–179, 1976, *Structural Concepts in Immunology and Immunochemistry*, (Holt, Rinehart and Winston, NY).

Leontein et. al., "Assignment of Absolute Configuration of Sugars by G.L.C. of their Acetylated Glycosides Formed From Chiral Alcohols", pp. 359–362, 1978, *Carbohydrate Research*, vol. 62.

Lindberg et. al., "Immunology and Immunochemistry of Synthetic and Semisynthetic *Salmonella* O–Antigen–Specific Glycoconjugates", pp. 83–118, 1983, in *Bacterial Lipopolsaccahrides—Structure, Synthesis and Biological Activities*, L. Anderson and F. M. Unger, eds., ACS Symposium Series, Wash. D.C.

Lindberg, et al., "Structural Studies of the O–Specific Side–Chain of the Lipopolysaccharide From *Escherichia coli* O 55", pp. 105–112, 1981, *Carbohydrate Research*, vol. 97.

Lu, et al., "Characterization and Application of a Murine Monoclonal Antibody that Reacts Specifically With the Serogroup $D_1$ *Salmonella*", pp. 135–140, 1991, *FEMS Microbiology Letters*, vol. 80.

Lüderitz et. al., "Immunochemistry of O and R Antigens of *Salmonella* and Related *Enterobacteriaceae*", pp. 192–255, 1966, *Bacteriological Reviews*, vol. 30.

Matsuhashi et. al., "Enzymatic Synthesis of Cytidine Diphosphate 3,6–Dideoxyhexoses", pp. 4267–4274, 1966, *The Journ. of Biol. Chem.*, vol. 241.

Matsuhashi, "Enzymatic Synthesis of Cytidine Diphosphate 3,6–Dideoxyhexoses", pp. 4275–4282, 1966, *The Journ. of Biol. Chem.*, vol. 241.

Matsuhashi et. al., "Enzymatic Synthesis of Cytidine Diphosphate 3,6–Dideoxyhexoses", pp. 4283–4287, 1966, *The Journal of Biol. Chem.*, vol. 241.

McBroom et al., "Carbohydrate Antigens: Coupling of Carbohydrates to Proteins by Dianzonium and Phenylisothiocyanate Reactions", pp. 212–219, 1972, *Methods in Enzymology*, vol. 28B.

Ruitenberg et al., "Reliability of the Enzyme–Linked Immunosorbent Assay (Elisa) for the Serodiagnosis of *Trichinella spiralis* Infections in Conventionally Raised Pigs", pp. 67–83, 1976, *Journ. of Immunological Methods*, vol. 10.

Russell et. al., "Synthesis of Stereospecifically Labeled 3,6–Dideoxyhexoses", pp. 95–114, 1990, *Carbohydrate, Research*, vol. 201.

Samuelsson, et. al., "Structure of O–Specific Side Chains of Lipopolysaccharides from *Yersinia pseudotuberculosis*", pp. 1010–1016, 1974, Journal of Bateriology, vol. 117, No. 3, Mar.

Sanford et. al., "The Structure of the *Aerobacter aerogenes* A3 (SI) Polysaccharide. I. A Reexamination Using Improved Procedures for Methylation Analysis", pp. 1508–1517, 1966, *Biochemistry*, vol. 5, May.

Silberstein et. al., "Antigens from *Trichinella spiralis* That Induce a Protective Response In The Mouse", pp. 898–904, 1984, *The Journ. of Immunology*, vol. 132, Feb.

Silberstein et. al., "Immunization With Purified Antigens Protects Mice From Lethal Infection With *Trichinella spiralis*", pp. 516–517, 1985, *The Journ. of Parasitology*, vol. 71, Aug.

Su et. al., "A Dot–Elisa Mimicry Western Blot Test for the Detection of Swine Trichinellosis", pp. 76–82, 1991, *J. Parasitol.*, vol. 77.

Su et. al., "Cloning and Expression of Complementary DNA Encoding an Antigen of *Trichinella spiralis*", pp. 331–336, 1991, *Molecular and Biochemical Parasitology*, vol. 45.

Sugane et. al., "Molecular Analysis of the Gene Encoding an Antigenic Polypeptide of *Trichinella spiralis* Infective Larvae", pp. 1–8, 1990, *J. Helminthology*, vol. 64.

Svenson et. al., "Coupling of Acid Labile *Salmonella* Specific Oligosaccharides to Macromolecular Carriers", pp. 323–335, 1979, *Journ. of Immunological Methods*, vol. 25.

Svenson et al., "Artificial *Salmonella* Vaccines: *Salmonella typhimurium* O–Antigen–Specific Oligo–saccharide—Protein Conjugates Elicit Protective Antibodies in Rabbits and Mice", pp. 490–496, 1981, *Infection and Immunity*, vol. 32, No. 1, May.

Svenson et al., "Artifical *Salmonella* Vaccines: O–Antigenic Oligosaccharide—Protein Conjugates Induce Protection Against Infection with *Salmonella typhimurium*", pp. 863–872, 1979, *Infection and Immunity*, vol. 25, No. 3, Sep.

Svenungsson et. al., "Synthetic Disaccharide—Protein Antigens for Production of Specific 04 and 09 Antisera for Immunofluorescence Diagnosis of Salmonella", pp. 1–11, 1977, *Med. Microbiol. Immunol.*, vol. 163.

Svenungsson, et al., "Diagnosis of Salmonella Infections: Specificity of Indirect Immunofluorescence for Rapid Identification of *Salmonella enteritidis* and Usefulness of Enzyme–Linked Immunosorbent Assay", pp. 927–936, 1979, *J. Infectious Disease*, vol. 140, No. 6, Dec.

Verma et. al., "Identification and Sequence of rfbS and rfbE, Which Determine Antigenic Specificity of Group A and Group D Salmonellae", pp. 5694–5701, 1989, *Journ. of Bacteriology*, vol. 171, Oct.

Waeghe et. al., "Determination, by Methylation Analysis, of the Glycosyl–Linkage Compositions of Microgram Quantities of Complex Carbohydrates", pp. 281–304, 1983, *Carbohydrate Research*, vol. 123.

Wyk et. al., "Identificaton and Sequence of the Gene for Abequose Synthase, Which Confers Antigenic Specificity on Group B Salmonellae: Homology With Galactose Epimerase", pp. 5687–5693, 1989, *J. Bacteriology*, vol. 171, Oct.

York et. al., Isolation and Characterization of Plant Cell Walls and Cell Wall Components", pp. 3–40, 1985, *Methods in Enzymology*, vol. 118.

Zarlenga et. al., "Molecular Cloning and Expression of an Immunodominant 53–kDa Excretory–Secretory Antigen From *Trichinella spiralis* Muscle Larvae", pp. 165–174, 1990, *Molecular and Biochemical Parasitology*, vol. 42.

CARBOHYDRATE-BASED VACCINE AND DIAGNOSTIC REAGENT FOR TRICHINOSIS

FIELD OF THE INVENTION

The present invention relates to novel carbohydrate-based vaccines and their use to protect animals from Trichinella infection. The present invention further relates to novel carbohydrate-based diagnostic reagents and their use to detect Trichinella infection in animals. The invention particularly relates to tyvelose-containing and fucose-containing vaccines to protect animals from trichinosis and to tyvelose-containing diagnostic reagents to detect *Trichinella spiralis* infection.

BACKGROUND OF THE INVENTION

Trichinosis is a disease of world-wide distribution that is primarily due to the ingestion of raw or undercooked meat (principally pork) containing the infective larval stage of *Trichinella spiralis*, the helminth parasite that causes the disease. After ingestion, *Trichinella spiralis* larvae infect the intestine where they mature within a few days. Female worms then bear newborn larvae which enter the general circulatory system and after several days accumulate in the striated muscles of the infected animal. Until recently, *Trichinella spiralis* infection has been detected by visual detection of larvae in muscle snips or digestion of muscle to liberate larvae (see, for example, U.S. Pat. No. 3,892,529 by Giles, issued Jul 1, 1975, and U.S. Pat. No. 3,918,818 by Giles, issued Nov. 11, 1975).

A group of protein (including glycoprotein) antigens extracted from *Trichinella spiralis* muscle stage larvae has been the subject of numerous studies in recent years, particularly in attempts to develop vaccines and diagnostic agents for trichinosis. These larval antigens are highly immunodominant and are apparently only present during the first muscle larval stage ($L_1$) of *Trichinella spiralis* infection, being found on both the cuticular surface and excretory/secretory (ES) products of $L_1$ larvae (see, for example, Denkers et al., pp. 241–250, 1990, *Mol. Biochem. Parasitol.*, Vol. 41). These larval antigens, designated TSL-1 antigens by Appleton et al., pp. 190–192, 1991, *Parasitol. Today*, Vol. 7, evoke a strong $IgG_1$ antibody response in mice following oral infection (see, for example, Denkers et al., pp. 3152–3159, 1990, *J. Immunol.*, Vol. 144) and induce substantial protection against challenge infections (see, for example, Silberstein et al., pp. 898–904, 1984, *J. Immunol.*, Vol. 132; Silberstein et al., pp. 516–517, 1985, *J. Parasitol.*, Vol. 71; Gamble, pp. 398–404, 1985, *Exp. Parasitol.*, Vol. 59; Gamble et al., pp. 2396–2399, 1986, *Am. J. Vet. Res.*, Vol. 47; Ortega-Pierres et al., pp. 563–567, 1989, *Parasitol. Res.*, Vol. 75; Denkers et al., *J. Immunol.*, ibid.; Jarvis et al., pp. 498–501, 1992, *Parasite Immunol.*, Vol. 14).

TSL-1 antigens migrate under reducing conditions on SDS-PAGE (sodium dodecyl sulfate polyacrylamide gel electrophoresis) in a molecular weight range of 40–70 kilodaltons (kDa). Denkers et al., *Mol. Biochem. Parasitol.*, ibid., have shown that at least six of the TSL-1 antigens share a common, highly immunodominant determinant. Use of monoclonal antibodies raised against the determinants indicated that the determinants are quite selective for *Trichinella spiralis* in that the monoclonal antibodies did not recognize other parasites, including the closely related species *Trichuris muris* (Denkers et al., pp. 403–410, 1991, *Exp. Parasitol.*, Vol. 72). Moreover, the determinants appear to be ubiquitous among all *Trichinella spiralis* isolates tested so far (see, for example, Denkers et al., *Exp. Parasitol.*, ibid.; Gamble et al., pp. 67–74, 1984, *Am. J. Vet. Res.*, Vol. 46; Gamble et al., pp. 379–389, 1984, *Vet. Immunol. Immunopath.*, Vol. 6).

TSL-1 antigens are believed to have both protein and carbohydrate immunoreactive determinants, although there is some conflict in the literature about the importance of each. Denkers, et al., *Mol. Biochem. Parasitol.*, ibid., demonstrated that the immunodominant determinants can be removed by treatment with trifluoromethanesulfonic acid, mild base, or N-glycanase, suggesting that the determinants are associated with both N-linked and O-linked carbohydrate groups. Denkers et al. also showed that the immunodominant determinants were not phosphorylcholine but did not further identify the composition of the carbohydrate moiety. Gold et al., pp. 187–196, *Mol. Biochem. Parasitol.*, Vol. 41, isolated TSL-1 antigens of 43 kDa and 45–50 kDa and treated them with N-glycanase. The deglycosylated antigens were no longer able to bind to polyclonal antibodies raised against the glycosylated versions of the proteins, again suggesting the importance of carbohydrate moieties, although Gold et al. do not exclude the possibility of peptide epitopes as well.

In contrast, Jarvis et al., ibid., concluded that protein epitopes alone could induce protective immunity to *Trichinella spiralis*, having shown that ES antigens that had been deglycosylated using sodium periodate were as effective as native ES antigens in protecting mice from *Trichinella spiralis* infection in both active and passive immune assays. Su et al., pp. 331–336, 1991, *Mol. Biochem. Parasitol.*, Vol. 45, reported that a recombinant fusion protein consisting of beta-galactosidase joined to the 49-kDa TSL-1 antigen (P49) produced in *Escherichia coli* was bound by antibodies contained in serum isolated from swine infected with *Trichinella spiralis*, and by antibodies contained in serum isolated from mice immunized with native P49 antigen, but was not recognized by three monoclonal antibodies that bind selectively to native P49 antigen. Su et al. concluded that such results suggest that, at least the P49 antigen has both protein and carbohydrate immunoreactive determinants.

Several investigators have developed enzyme-linked immunosorbent assays (ELISAs) to detect *Trichinella spiralis* infection using a variety of reagents, such as, crude *Trichinella spiralis* parasite preparations, partially purified ES antigen preparations, and monoclonal antibodies raised against, for example, the ES immunodominant determinants (see, for example, Ruitenberg et al., pp. 67–83, 1976, *J. Immunol. Methods*, Vol. 10; Gamble et al., 1983, pp. 349–361, *Vet. Parasitol.*, Vol. 13; Gamble et al., *Am. J. Vet. Res.*, ibid.; Gamble et al., *Vet. Immunol. Immunopath.*, ibid.; U.S. Pat. No. 4,670,384, by Gamble et al., issued Jun. 2, 1987). Assays based on undefined crude or semi-defined antigen preparations are problematic due to false-positive and false-negative reactions as well as to cross-reactivity with antibodies corresponding to antigens of other parasites. Monoclonal antibody-based or purified protein-based assays, while often leading to fewer false-positive or false-negative reactions, can still have specificity and selectivity problems, in addition to difficulties of producing such components without batch-to-batch variation, and of maintaining the stability of the components.

U.S. Pat. No. 4,795,633, by Murrell et al., issued Jan. 3, 1989, discloses a swine trichinosis vaccine consisting of an inert newborn larvae preparation emulsified with an adjuvant. GB 1,580,539, published Dec. 3, 1989, discloses a trichinosis vaccine containing ES antigens of *Trichinella*

*spiralis* muscle stage larvae. Several groups of investigators have reported the cloning of at least portions of certain *Trichinella spiralis* antigen genes with the goal of developing defined diagnostics reagents and/or vaccines (see, for example, Su et al., *Mol. Biochem. Parasitol.*, ibid.; Sugane et al., pp. 1–8, 1990, *J. Helminth.*, Vol. 64; Zarlenga et al., pp. 165–174, 1990, *Mol. Biochem. Parasitol.*, Vol. 42). Problems with protein-based vaccines, and particularly with recombinant protein-based vaccines, include difficulty of preparation (particularly with respect to removal of harmful contaminants), lack of stability, potential reduced antigenicity compared to the native protein, and potential autoimmune reactions due to similarities between parasite and animal host proteins (e.g., *Brugia pahangi* glutathione peroxidase and *Dirofilaria immitis* superoxide dismutase; see, for example, Callahan et al., 235–252, 1991, *Mol. Biochem. Parasitol.*, Vol. 49).

A number of anthelminthic drugs have been developed to treat trichinosis (see, for example, U.S. Pat. No. 5,140,042 by Arison et al., issued Aug. 18, 1992; U.S. Pat. No. 5,089,530 by Tsipouras et al., issued Feb. 18, 1992; U.S. Pat. No. 5,073,567, by Maeda et al., issued Dec. 17, 1991; U.S. Pat. No. 5,008,250, by Fisher et al., issued Apr. 16, 1991; and U.S. Pat. No. 4,833,168, by Wyvratt, issued May 23, 1989). Such drugs, however, apparently cannot be used to prevent trichinosis, are expensive to produce, usually have undesirable side effects, and are not always effective.

There remains a need for both diagnostic reagents to detect *Trichinella spiralis* infection and for vaccines and other drugs to protect animals from trichinosis that have improved specificity, selectivity, stability, consistency, and ease of use.

SUMMARY OF THE INVENTION

The present invention relates to a vaccine capable of protecting an animal from Trichinella infection, and preferably from trichinosis caused by *Trichinella spiralis* infection, when the vaccine is administered to the animal in an effective amount. One embodiment is a vaccine that includes at least one tyvelose-containing oligosaccharide or functional equivalent thereof, the tyvelose-containing oligosaccharide being selected from the group consisting of tyvelose and tyvelose joined through glycosidic linkage to at least one monosaccharide. Another embodiment is a vaccine that includes at least one fucose-containing oligosaccharide or functional equivalent thereof, the fucose-containing oligosaccharide being selected from the group consisting of fucose and fucose joined through glycosidic linkage to at least one monosaccharide. Vaccines of the present invention can also include both tyvelose-containing oligosaccharides and fucose-containing oligosaccharides. Preferred monosaccharides to join to either tyvelose or fucose include tyvelose, fucose, mannose, N-acetylgalactosamine, and N-acetylglucosamine. Tyvelose-containing oligosaccharides preferably have at least one tyvelose terminal residue, and fucose-containing oligosaccharides preferably have at least one fucose terminal residue. Preferred vaccines contain tyvelose-containing disaccharides and/or fucose-containing disaccharides.

Vaccines of the present invention preferably include tyvelose-containing oligosaccharides and/or fucose-containing oligosaccharides conjugated to an effective carrier. Vaccines of the present invention can also include at least one immunopotentiator.

Vaccines of the present invention can protect animals by, for example, preventing infection by Trichinella or by ameliorating or treating disease caused by the parasite. In one embodiment, the vaccines are also capable of protecting the animal from infection by other organisms containing tyvelose antigenic epitopes such as Salmonella serogroup D and *Yersinia pseudotuberculosis* serogroup IV microorganisms. Preferred animals to vaccinate include mammals, preferably pigs and humans, and particularly pigs.

The present invention also includes a method to protect an animal from Trichinella infection, and preferably trichinosis, by administering to the animal an effective amount of a vaccine of the present invention.

The present invention furthermore relates to a diagnostic reagent effective in detecting Trichinella infection, and preferably *Trichinella spiralis* infection. The diagnostic reagent includes at least one tyvelose-containing oligosaccharide or functional equivalent thereof, the tyvelose-containing oligosaccharide being selected from the group consisting of tyvelose and tyvelose joined through glycosidic linkage to at least one monosaccharide, which preferably is selected from the group consisting of tyvelose, fucose, mannose, N-acetylgalactosamine, and N-acetylglucosamine. Tyvelose-containing oligosaccharides preferably have at least one tyvelose terminal residue, and preferably are disaccharides. One embodiment of the present invention is a diagnostic reagent that includes a tyvelose-containing oligosaccharide conjugated to an effective carrier.

Another embodiment of the present invention is a method to determine Trichinella, and preferably *Trichinella spiralis*, infection in an animal which includes: (a) applying serum collected from the animal onto a surface coated with a diagnostic reagent of the present invention under conditions such that selective binding of an antibody from the serum indicative of Trichinella infection to the reagent-coated surface results in the formation of a selective binding complex on the reagent-coated surface; (b) removing non-bound serum material under conditions that retain the selective binding complex on the reagent-coated surface; and (c) determining Trichinella infection by detecting the selective binding complex. The step of detecting preferably includes (a) contacting the selective binding complex with an identifying labeled compound capable of binding selectively to the antibody or to the complex; (b) removing substantially all of the identifying labeled compound that does not selectively bind to the antibody or to the complex; and (c) detecting the identifying labeled compound, wherein presence of the labeled compound is indicative of Trichinella infection. Also disclosed is a method to discriminate between Trichinella infection and infection caused by Salmonella serogroup D microorganisms and/or *Yersinia pseudotuberculosis* serogroup IV microorganisms that includes the use of fucose-containing oligosaccharides of the present invention.

The invention also provides a diagnostic kit for detecting Trichinella, and preferably *Trichinella spiralis*, infection in an animal that includes a diagnostic reagent of the present invention. The kit can also include a surface capable of being coated with the reagent. Preferably the surface is pre-coated the reagent. The kit can also include a means for detecting the binding of an antibody indicative of Trichinella infection to the reagent. The kit can also include an agent capable of discriminating between Trichinella infection and an infection caused by Salmonella serogroup D and/or *Yersinia pseudotuberculosis* microorganisms.

Animals that can be diagnosed using diagnostic reagents and diagnostic kits of the present invention include mammals, preferably humans and pigs, and particularly pigs.

One embodiment of the present invention is a vaccine including at least one tyvelose-containing oligosaccharide or functional equivalent thereof, the tyvelose-containing oligosaccharide being selected from the group consisting of tyvelose and tyvelose joined through glycosidic linkage to at least one monosaccharide, the oligosaccharide having at least one tyvelose terminal residue that is joined through glycosidic linkage to a monosaccharide other than mannose.

Another embodiment of the present invention is an antibody, or functional equivalent thereof, capable of selectively binding to a Trichinella parasite, the antibody being produced by a process comprising: (a) administering to an animal an effective amount of a vaccine of the present invention; and (b) recovering the antibody. Antibodies of the present invention can be either polyclonal or monoclonal antibodies. Such antibodies or functional equivalents thereof can be used to protect an animal from Trichinella infection, such as from trichinosis, by administering to the animal an amount of the antibody or functional equivalent thereof effective to protect the animal from trichinosis. Such antibodies or functional equivalents thereof can also be used to diagnose Trichinella infection in an animal.

Yet another embodiment is an antibody of the present invention that is conjugated to a cytotoxic agent that can be used to protect an animal from Trichinella infection, and preferably from trichinosis.

An additional embodiment is an anti-*Trichinella spiralis* drug capable of substantially inhibiting tyvelose production by *Trichinella spiralis* or other Trichinella parasites, the drug being capable of substantially inhibiting at least one enzyme essentially specific for tyvelose biosynthesis, thereby protecting an animal from Trichinella infection, and preferably from trichinosis.

DETAILED DESCRIPTION OF THE INVENTION

The present invention includes vaccines and diagnostic reagents, preferably directed against Trichinella, and even more preferably directed against *Trichinella spiralis*, infection that contain tyvelose (i.e., 3,6-dideoxy-D-arabinohexose) predicated upon the inventors' surprising discovery that the immunodominant determinants of TSL-1 antigens contain significant amounts of tyvelose, an extremely rare sugar in nature. As such, vaccines and diagnostic reagents of the present invention are advantageous because they are highly selective, particularly for *Trichinella spiralis* (i.e., they specifically target *Trichinella spiralis* and do not substantially recognize other organisms).

Tyvelose has, to the inventors' knowledge, not previously been found in eukaryotes and has not previously been found associated with a protein (i.e., as a component of a glycoprotein). In fact, 3,6-dideoxyhexoses as a class are quite rare, having only been identified in ascaryl alcohols (i.e., ascarosides) of the eggs of the worm parasite Ascaris and in certain gram negative bacterial lipopolysaccharides (see, for example, Fairbairn, pp. 491–554, 1957, *Exp. Parasitol.*, Vol. 6; Jezyk et al., pp. 691–705, 1967, *Comp. Biochem. Physiol.*, Vol. 23; Lindberg et al., pp. 83–118, 1983, in *Bacterial Lipopolysaccharides–Structure, Synthesis and Biological Activities*, L. Anderson and F. M. Unger, eds., ACS Symposium Series, Washington, D.C.; and references cited therein). Ascaris eggs contain ascarylose, or 3,6-dideoxy-L-arabinohexose, which is immunologically distinct from tyvelose. The 3,6-dideoxyhexoses contained in bacterial lipopolysaccharides have been particularly well studied in Salmonella, a bacterial genus that has been serotyped essentially according to the nature of its 3,6-dideoxyhexose determinants. For example, the lipopolysaccharides of Salmonella serogroup A contain paratose, those of serogroup B contain abequose, and those of serogroup D contain tyvelose. Although the 3,6-dideoxyhexoses are part of a repeating unit of 3 to 5 monosaccharides, it has been shown that immune responses to Salmonella lipopolysaccharide antigens are dominated by 3,6-dideoxyhexose-based epitopes (see, for example, Lindberg et al., ibid.; Luderitz et al., pp. 192–255, 1966, Bacteriol. Rev., Vol. 30). Similarly, *Yersinia* (i.e., Pasteurella) *pseudotuberculosis* microorganisms have been serotyped based on whether the bacteria contain paratose (serogroups I and III), abequose (serogroup II), tyvelose (serogroup IV), or ascarylose (serogroup V) (see, for example, Luderitz et al., ibid.).

That investigators would not have expected tyvelose to be present on *Trichinella spiralis* antigens is underscored by the study of Jarvis et al., ibid., in which Jarvis et al. concluded that peptide epitopes, rather than carbohydrate epitopes, were responsible for the antigenicity of periodate-treated ES antigens. This conclusion was reached in spite of reports in the literature that 3,6-dideoxyhexoses are resistant to cleavage by periodate, a characteristic that has been used to verify Salmonella serotyping (see, for example, Kabat, pp. 176–179, 1976, *Structural Concepts in Immunology and Immunochemistry*, Holt, Rinehart and Winston, New York). Clearly, Jarvis et al. did not recognize that tyvelose was a component of *Trichinella spiralis* immunodominant determinants.

The inventors have also identified four other monosaccharides that comprise a substantial proportion of *Trichinella spiralis* TSL-1 immunodominant determinants: fucose, mannose, N-acetylgalactosamine, and N-acetylglucosamine, with the amount of fucose present being surprisingly high. Fucose, although prevalent in nature, is not usually a dominant sugar in the overall composition. Fucose has also been shown to have immunological relevance in mammals and parasites, having been found associated with several particular parasites and with glycosphingolipids in certain mammalian tumor tissues. As such, fucose-based vaccines of the present invention are also believed to be advantageous for protecting an animal from trichinosis.

One embodiment of the present invention is a vaccine that includes at least one tyvelose-containing oligosaccharide or functional equivalent thereof, the vaccine being capable of protecting an animal from Trichinella infection, and preferably from trichinosis caused by *Trichinella spiralis* infection when administered to the animal in an effective amount. As used herein, a vaccine "capable of protecting an animal from Trichinella infection" refers to the ability of the vaccine to treat (e.g., as an immunotherapeutic agent), ameliorate, and/or prevent Trichinella infection caused by a Trichinella parasite that contains tyvelose antigenic epitopes (i.e., epitopes that are able to bind to antibodies produced upon administration of a tyvelose-containing oligosaccharide vaccine of the present invention). As used herein, a vaccine "capable of protecting an animal from trichinosis" refers to the ability of the vaccine to treat (e.g., as an immunotherapeutic agent), ameliorate, and/or prevent *Trichinella spiralis* infection that otherwise would lead to trichinosis in the animal. Preferably the vaccine protects the animal by eliciting an immune response. A preferred vaccine is one that, when administered to an animal, is able to elicit (i.e., stimulate) the production of high antibody titers as well as a high-level cellular immune response capable of protecting the animal from trichinosis.

As used herein, a "tyvelose-containing oligosaccharide" can be a single tyvelose or tyvelose joined through glycosidic linkage to at least one monosaccharide. Preferred monosaccharides include tyvelose, fucose, mannose, N-acetylgalactosamine, and N-acetylglucosamine. Preferably, the tyvelose-containing oligosaccharide has at least one tyvelose terminal residue. As used herein, "tyvelose joined through glycosidic linkage to at least one of the following monosaccharides" denotes an oligosaccharide in which tyvelose is joined to one or more monosaccharides according to standard carbohydrate chemistry (i.e., by glycosidic linkages). As such, the oligosaccharide can be either linear or branched. The inventors have found that tyvelose is apparently almost always located at the non-reducing terminal position of TSL-1 immunodominant determinants; i.e., that tyvelose is believed to be principally a terminal residue of naturally-occurring oligosaccharides on TSL-1 antigens. As used herein, a "terminal residue" is located either at an end (terminus) of or at a branch-point of an oligosaccharide such that the residue is exposed to elicit an immune response capable of protecting an animal from trichinosis and/or to bind (i.e., adsorb) selectively to an antibody indicative of *Trichinella spiralis* infection.

As used herein, a functional equivalent of a tyvelose-containing oligosaccharide is a molecule (e.g., a carbohydrate or other organic molecule) that has an epitope that can essentially mimic the tyvelose-containing oligosaccharide's epitope by eliciting a substantially similar immune response. Preferably the functional equivalent has a similar tertiary structure to the oligosaccharide's epitope. As such, functional equivalents of tyvelose may be determined, for example, either by analyzing molecules sharing a substantially similar epitope structure as that of naturally occurring tyvelose or by selecting those molecules with substantially similar functional identifying characteristics.

Another embodiment of the present invention is a vaccine that includes at least one fucose-containing oligosaccharide or functional equivalent thereof, the vaccine being capable of eliciting an immune response capable of protecting an animal from Trichinella infection, and preferably from trichinosis caused by *Trichinella spiralis* infection, when administered in an effective amount. As used herein, a "fucose-containing oligosaccharide" can be a single fucose or fucose joined through glycosidic linkage to at least one monosaccharide. Preferred monosaccharides include tyvelose, fucose, mannose, N-acetylgalactosamine, and N-acetylglucosamine. Preferably, the fucose-containing oligosaccharide has at least one fucose terminal residue. The inventors have found that the fucose moieties present on *Trichinella spiralis* immunodominant determinants are primarily non-reducing terminal residues. As used herein, a functional equivalent of a fucose-containing oligosaccharide is a molecule (e.g., a carbohydrate or other organic molecule) that has an epitope that can essentially mimic the fucose-containing oligosaccharide's epitope by eliciting a substantially similar immune response. Preferably the functional equivalent has a similar tertiary structure to the oligosaccharide's epitope. As such, functional equivalents of fucose may be determined, for example, either by analyzing molecules sharing a substantially similar epitope structure as that of naturally occurring fucose or by selecting those molecules with substantially similar functional identifying characteristics.

Preferred tyvelose-containing oligosaccharides of the present invention include tyvelose, and tyvelose joined to from about one to about three monosaccharides, with disaccharide oligosaccharides being more preferred. Similarly, preferred fucose-containing oligosaccharides of the present invention include fucose, and fucose joined to from about one to about three monosaccharides, with disaccharide oligosaccharides being more preferred. It is however, within the scope of the invention that larger oligosaccharides having at least one tyvelose terminal residue and/or at least one fucose terminal residue can also be effective vaccines. Particularly preferred vaccine contain the disaccharide tyvelose--tyvelose, tyvelose--fucose, tyvelose--mannose, tyvelose--N-acetylgalactosamine, tyvelose--N-acetylglucosamine, fucose--fucose, fucose--mannose, fucose--N-acetylgalactosamine, fucose--N-acetylglucosamine, or mixtures of those disaccharides. As used herein "--" in this context indicates the glycosidic linkage that forms the disaccharide. Without being bound by theory, the inventors believe that disaccharide vaccines against trichinosis can be equally effective as disaccharide vaccines against Salmonella, which are described, for example, in Svenungsson et al., pp. 1–11, 1977, *Med. Microbiol. Immunol.*, Vol. 163; in Lindberg et al., ibid.,; and in references cited therein. The inventors further believe that tyvelose particularly is likely to make an effective vaccine since tyvelose, like other 3,6-dideoxyhexoses, is a dominant antigenic determinant.

A preferred vaccine of the present invention comprises a tyvelose-containing oligosaccharide conjugated to an effective carrier. Another preferred vaccine has a fucose-containing oligosaccharide conjugated to an effective carrier. As used herein, an "effective carrier" is a compound that enables the oligosaccharide to function as a vaccine or diagnostic agent and that is conjugated to the oligosaccharide in such a manner as to not substantially interfere with the oligosaccharide's desired function. Preferably, the carrier is able to augment, or enhance, the oligosaccharide's activity as a vaccine or diagnostic reagent. As used herein, "conjugated" refers to joining the carbohydrate moiety and carrier together, preferably by a covalent attachment. For example, in fucose or tyvelose vaccines, the carrier is attached to tyvelose or fucose in such a manner that the tyvelose or fucose epitope maintains the capacity to elicit an immune response capable of protecting an animal from trichinosis or to selectively bind to an antibody indicative of *Trichinella spiralis* infection. When the vaccine is a disaccharide or larger oligosaccharide, the carrier is typically attached to a monosaccharide other than the tyvelose or fucose epitope in order to reduce potential interference with the ability of the oligosaccharide to function as an effective vaccine or diagnostic reagent. Particularly preferred vaccines include tyvelose::carrier, tyvelose--tyvelose::carrier, tyvelose--fucose::carrier, tyvelose--mannose::carrier, tyvelose--N-acetylgalactosamine::carrier, tyvelose--N-acetylglucosamine::carrier, fucose::carrier, fucose--fucose-::carrier, fucose--mannose::carrier, fucose--N-acetylgalactosamine::carrier, fucose--N-acetylglucosamine::carrier, or mixtures thereof, wherein "::" indicates the attachment of the carrier to the disaccharide.

A preferred carrier is a compound of sufficient size and immunogenicity capable of augmenting the immune response of the vaccine. Suitable carriers include, but are not limited to: proteins, such as toxoids, serum proteins, keyhole limpet hemocyanin, or *Trichinella spiralis* muscle stage larval antigens; polymerized sugars, such as polydextrans; other polymers; viruses or viral subunits; and lipid-containing compounds, such as liposomes. Preferred carriers of the present invention include bacterial toxoids, such as tetanus toxoid, diphtheria toxoid, and cholera toxoid; bovine serum albumin; ovalbumin; and *Trichinella spiralis* muscle stage larval antigens. A particularly preferred carrier is tetanus toxoid, which has been shown to be safe in vaccine applications (see, for example, Herrington et al., pp. 257–259, 1987, *Nature*, Vol. 328).

Another particularly preferred class of carriers consists of *Trichinella spiralis* antigen carriers, defined herein as *Trichinella spiralis* muscle stage larval antigens (as heretofore described), recombinant protein antigens corresponding to those antigens, and functional equivalents of the larval antigens or corresponding recombinant protein antigens (e.g., that elicit at least some immunogenic response against trichinosis). A vaccine comprising at least one *Trichinella spiralis* antigen carrier conjugated to a tyvelose-containing or fucose-containing oligosaccharide of the present invention may afford animals enhanced protection compared to either the larval antigen or oligosaccharide alone.

One embodiment of the present invention is a vaccine containing more than one tyvelose- or fucose-containing oligosaccharide. Although a single type of oligosaccharide is believed capable of eliciting an immune response, it is likely that a mixture of various types of oligosaccharides of the present invention may be more efficacious. Preferably the various types of oligosaccharides of the present invention are conjugated to effective carriers, as heretofore described.

Another embodiment of the present invention is the inclusion of at least one fucose-containing oligosaccharide in tyvelose-containing oligosaccharide vaccines of the present invention. Yet another embodiment of the present invention is the inclusion of at least one tyvelose-containing oligosaccharide in fucose-containing oligosaccharide vaccines of the present invention. Mixtures of fucose-containing oligosaccharides and tyvelose-containing oligosaccharides are believed to enhance the ability of such a vaccine to protect an animal from trichinosis. While not being bound by theory, it is believed that the prevalence of fucose and tyvelose moieties as non-reducing terminal residues in *Trichinella spiralis* immunodominant determinants suggests that each structure is likely to possess a dominant epitope that is able to elicit an immune response that is capable of protecting an animal from trichinosis.

Another embodiment of the present invention is a vaccine including at least one tyvelose-containing oligosaccharide having at least one tyvelose terminal residue joined through glycosidic linkage to a monosaccharide other than mannose.

Yet another aspect of the present invention is the realization that the claimed tyvelose-containing oligosaccharide vaccines of the present invention are also capable of protecting animals from infection by Salmonella or *Yersinia pseudotuberculosis* microorganisms that have lipopolysaccharides containing tyvelose, e.g., Salmonella serogroup D or *Yersinia pseudotuberculosis* serogroup IV microorganisms. Thus, vaccines of the present invention may be used to simultaneously protect animals from Salmonella serogroup D, *Yersinia pseudotuberculosis* serogroup IV and *Trichinella spiralis* infections.

Furthermore, it is within the scope of the present invention that tyvelose-containing oligosaccharide vaccines of the present invention can be used to protect an animal against infection by any parasite of the genus Trichinella, and even more broadly against infection by any organism, that contains tyvelose antigenic epitopes (i.e., epitopes that can be bound by antibodies produced upon administration of a tyvelose-containing oligosaccharide vaccine of the present invention). Similarly, it is within the scope of the present invention that fucose-containing oligosaccharide vaccines of the present invention can be used to protect an animal against infection by any parasite of the genus Trichinella, and even more broadly against infection by any organism, that contains fucose antigenic epitopes (i.e., epitopes that are able to bind to antibodies produced upon administration of a fucose-containing oligosaccharide vaccine of the present invention).

Vaccines of the present invention can also include additional antigenic compounds effective in eliciting an immune response against, for example, other stages of the Trichinella life cycle. Vaccines of the present invention can also be components of multiple vaccine preparations that include antigens targeted against more than one disease.

Vaccines of the present invention can be produced using standard techniques of carbohydrate and protein linkage technologies (see, for example, Lindberg et al., ibid.; Russell et al., pp. 95–114, 1990, *Carbohydrate Research*, Vol. 201; Svenson and Lindberg, pp. 323–335, 1979, *J. Immunol. Methods*, Vol. 25; McBroom et al., pp. 212–219, 1972, *Methods in Enzymology*, Vol. 28B). Briefly, the monosaccharides are produced and, as necessary for specific vaccine embodiments, joined by glycosidic linkage to form disaccharides and larger oligosaccharides. For preferred embodiments, the carbohydrate moieties are conjugated to effective carriers, preferably using reactive group linking agents. For example, one method to produce a vaccine containing tyvelose--mannose::tetanus toxoid includes the steps of (a) synthesizing tyvelose precursors, (b) joining the precursors to derivatized mannose residues, (c) joining the synthesized disaccharide to a suitable aglycone-containing reactive group, and (d) conjugating the modified disaccharide to a tetanus toxoid. One advantage of the present invention is the ease with which such carbohydrate-based vaccines can be produced on a consistent basis, particularly as compared with the time and effort required to produce recombinant protein-based vaccines. In addition, it may be particularly difficult to produce recombinant *Trichinella spiralis* proteins having tyvelose-containing epitopes using conventional recombinant techniques since (a) bacteria do not glycosylate proteins and (b) no eukaryotic cells are known to the inventors that are capable of producing tyvelose, except *Trichinella spiralis*.

Tyvelose- and fucose-containing oligosaccharide vaccines of the present invention are preferably recovered in "substantially pure" form. As used herein, "substantially pure" refers to a purity that allows for the effective use of the vaccine without substantial negative side effects. For example, substantially pure vaccines would not elicit undesired biological reactions when administered to animals to be treated.

Vaccines of the present invention can be administered to any animal, preferably to mammals, more preferably to humans and pigs, and particularly to pigs.

Vaccines can be formulated in an aqueous balanced salt solution that the animal to be vaccinated can tolerate. The vaccine can also include an immunopotentiator, such as an adjuvant or other agent that enhances the immune response of the vaccine. Suitable immunopotentiators include, but are not limited to, polymeric controlled release formulations, biodegradable implants, liposomes, bacterial preparations (such as bacterial coat proteins), viruses or viral proteins (such as coat proteins), oils, esters, glycols, Freund's adjuvant, aluminum-based salts, calcium-based salts, silica, polynucleotides, gamma interferon, Ribi adjuvants (available from Ribi ImmunoChem Research, Inc., Hamilton, Mont.), and saponins and their derivatives, such as Quil A (available from Superfos Biosector A/S, Denmark).

In order to protect animals from trichinosis, a vaccine of the present invention is administered in an effective amount, wherein an "effective amount" is an amount that allows the animal to produce a sufficient immune response to protect itself from trichinosis. Vaccines of the present invention can be administered to animals prior to infection by *Trichinella spiralis* to prevent trichinosis. Vaccines of the present invention can also be administered to animals after infection by *Trichinella spiralis* in order to treat the disease, in which case the vaccine is acting as an immunotherapeutic agent. Vaccines of the present invention are advantageous because they are stable and are easy to use, particularly in the field. Acceptable administration protocols include individual dose size, number of doses, frequency of dose administration, and mode of administration. A suitable single dose of the vaccine is a dose that is capable of protecting an animal from trichinosis when administered one or more times over a suitable time period. A preferred single dose of the vaccine is from about 1 microgram (µg) to about 1 milligram (mg) of the vaccine per kilogram (kg) body weight of the animal. Booster vaccinations can be administered from about 2 weeks to several years after the original vaccination. Preferably booster vaccinations are administered when the immune response of the animal becomes insufficient to protect the animal from trichinosis. A preferred administration schedule is one in which from about 1 µg to about 1 mg of the vaccine per kg body weight of the animal are administered from about one to about two times over a time period of from about 2 weeks to about 12 months. Modes of administration can include, but are not limited to, subcutaneous, intradermal, intravenous, nasal, oral, transdermal and intramuscular routes.

The efficacy of a vaccine of the present invention to protect an animal from trichinosis can be tested in a variety of ways including, but not limited to, detection of protective antibodies (using, for example, diagnostic reagents of the present invention), detection of cellular immunity within the vaccinated animal, or challenge of the vaccinated animal with *Trichinella spiralis* or antigens thereof to determine whether the vaccinated animal is resistant to trichinosis.

Another embodiment of the present invention relates to the production and use of antibodies, or functional equivalents of such antibodies, that are capable of selectively binding to *Trichinella spiralis* muscle stage larvae produced by an animal in response to administration of a vaccine of the present invention. Such antibodies can be either polyclonal or monoclonal antibodies. As used herein, functional equivalents of such antibodies are antibodies, including fragments of any size, that have similar selective epitope binding characteristics as the antibodies produced in response to vaccination. Antibodies produced by animals vaccinated with a vaccine containing tyvelose-containing oligosaccharides can bind selectively to tyvelose-containing epitopes. Similarly, antibodies produced by animals vaccinated with a vaccine containing fucose-containing oligosaccharides can bind selectively to fucose-containing epitopes. Antibodies of the present invention, including functional equivalents thereof, have a variety of potential uses that are within the scope of the present invention. For example, such antibodies can be used (a) as vaccines to passively immunize an animal in order to protect the animal from trichinosis, (b) as reagents in assays to detect *Trichinella spiralis* larvae or antigens thereof, and/or (c) as tools to recover *Trichinella spiralis* antigens having immunodominant determinants from a mixture of proteins and other contaminants.

Furthermore, antibodies of the present invention, including functional equivalents thereof, can be used to target cytotoxic agents to *Trichinella spiralis* larvae and larval antigens in order to directly kill the larvae or cells expressing larval antigens on their cell surface. Targeting can be accomplished by conjugating (i.e., stably joining) such antibodies to the cytotoxic agents. Suitable cytotoxic agents include, but are not limited to: double-chain toxins (i.e., toxins having A and B chains), such as diphtheria toxin, ricin toxin, Pseudomonas exotoxin, modeccin toxin, abrin toxin, and shiga toxin; single-chain toxins, such as pokeweed antiviral protein, α-amanitin, and ribosome inhibiting proteins; and chemical toxins, such as melphalan, methotrexate, nitrogen mustard, doxorubicin and daunomycin. Preferred double-chain toxins are modified to include the toxic domain and translocation domain of the toxin but to lack the toxin's intrinsic cell binding domain.

One embodiment of the present invention is a diagnostic reagent effective in detecting Trichinella, and particularly *Trichinella spiralis*, infection in an animal. A diagnostic reagent of the present invention includes at least one tyvelose-containing oligosaccharide that is capable of selectively binding to an antibody indicative of infection by the parasite. As heretofore defined, a "tyvelose-containing oligosaccharide" can be tyvelose or tyvelose joined through glycosidic linkage to at least one monosaccharide, preferably such that the tyvelose-containing oligosaccharide has at least one tyvelose terminal residue. Preferred monosaccharides include tyvelose, fucose, mannose, N-acetylgalactosamine, and N-acetylglucosamine.

Diagnostic reagents of the present invention, being based on the rare sugar tyvelose, are particularly advantageous because they exhibit great selectivity for *Trichinella spiralis* and other Trichinella parasites having tyvelose-containing epitopes in that they selectively bind to antibodies indicative of infection by such Trichinella parasites, and preferably by *Trichinella spiralis*. Preferred diagnostic reagents bind to antibodies raised by the animal in response to *Trichinella spiralis* infection but do not appreciably bind to antibodies directed against agents that do not have substantial amounts of tyvelose-containing epitopes. Thus, diagnostic reagents of the present invention are much less likely to give false-positive or false-negative reactions than are known diagnostic reagents, such as those heretofore described. Two possible exceptions are antibodies produced in response to infection by Salmonella serogroup D microorganisms or *Yersinia pseudotuberculosis* serogroup IV microorganisms since the antigens of these bacterial serogroups are the only antigens, other than TSL-1 antigens, known by the inventors to include tyvelose. It should be noted that all diagnostic reagents based on *Trichinella spiralis* TSL-1 immunodominant determinants, regardless of whether they are antigen- or antibody-based, are vulnerable to the same potential complications (e.g., false-positive reactions). Until the present invention, such a concern was unappreciated by those skilled-in-the art. Agents including fucose-containing oligosaccharides that are capable of eliciting an immune response to protect an animal against trichinosis may be used to discriminate between *Trichinella spiralis* and Salmonella serogroup D or *Yersinia pseudotuberculosis* serogroup IV infections, since neither Salmonella serogroup D nor *Yersinia pseudotuberculosis* serogroup IV lipopolysaccharides contain fucose. Alternatively, an antibody, preferably a monoclonal antibody, raised against the protein portion of *Trichinella spiralis* muscle larval antigens could be used to discriminate between *Trichinella spiralis* and Salmonella serogroup D or *Yersinia pseudotuberculosis* serogroup IV infections.

It is also within the scope of the present invention that diagnostic reagents of the present invention could be used to detect Salmonella serogroup D or *Yersinia pseudotubercu-*

*losis* serogroup IV infections, or any infections caused by organisms having tyvelose antigenic epitopes.

Diagnostic reagents of the present invention are also advantageous because, as described above for vaccines, the tyvelose-containing oligosaccharides and tyvelose-containing oligosaccharides conjugated to effective carriers are stable, are easy to produce on a consistent basis, and are easy to use, particularly in field tests. Previous assays for trichinosis, regardless of whether they were competitive or non-competitive in nature, and whether they were based on crude or partially purified *Trichinella spiralis* larval antigen preparations, polyclonal antibodies, and/or monoclonal antibodies have been hampered by several problems, including selectivity (i.e., large numbers of false-positive or false-negative reactions), ease of preparation, and/or usefulness in field tests (reviewed in, for example, Su et al., pp. 76–82, 1991, *J. Parasitol.*, Vol. 77).

Tyvelose-containing oligosaccharides used in vaccines of the present invention are also suitable for use as diagnostic reagents. As such, the method to produce tyvelose-containing oligosaccharides for diagnostic reagents is similar to that heretofore disclosed for the production of such oligosaccharide for vaccines. Preferred tyvelose-containing oligosaccharides include tyvelose, and tyvelose joined to from about one to about three monosaccharides, with disaccharide oligosaccharides being more preferred. Particularly preferred diagnostic reagents contain the disaccharide tyvelose--tyvelose, tyvelose--fucose, tyvelose--mannose, tyvelose--N-acetylgalactosamine, tyvelose--N-acetylglucosamine, or mixtures of such disaccharides.

One embodiment of the present invention is a diagnostic reagent in which the tyvelose-containing oligosaccharide is conjugated to an effective carrier in such a manner as to not substantially interfere with the ability of the reagent to selectively bind to antibodies indicative of *Trichinella spiralis* infection. Such a carrier may be useful in coating a diagnostic reagent to a surface for use in a diagnostic assay for trichinosis. The method and manner in which carriers are attached to diagnostic reagent oligosaccharides is similar to that heretofore disclosed for vaccine oligosaccharides. Preferred diagnostic reagents conjugated to a carrier include tyvelose::carrier, tyvelose--tyvelose::carrier, tyvelose--fucose::carrier, tyvelose--mannose::carrier, tyvelose--N-acetylgalactosamine::carrier, tyvelose--N-acetylglucosamine::carrier, or mixtures thereof.

Suitable and preferred carriers for tyvelose-containing oligosaccharide-based diagnostic reagents are as heretofore disclosed for tyvelose-containing oligosaccharide-based vaccines.

One embodiment of the present invention is a diagnostic reagent containing more than one tyvelose-containing oligosaccharide. Although a single oligosaccharide is capable of selectively binding to an antibody indicative of *Trichinella spiralis* infection, it is likely that a mixture of oligosaccharides may be more efficacious. Preferably the oligosaccharides are conjugated to effective carriers, as heretofore described.

Another embodiment of the present invention is the use of a diagnostic reagent of the present invention to detect *Trichinella spiralis* infection in an animal (i.e., a method to determine *Trichinella spiralis* infection in an animal using such a diagnostic reagent). Any animal susceptible to *Trichinella spiralis* infection can be tested, including, but not limited to humans and pigs. The detection method of the present invention is particularly useful in field tests, such as those conducted on pigs.

Any suitable assay can be used in which at least one diagnostic reagent of the present invention can be contacted with animal serum under conditions that allow for selective binding of the diagnostic reagent to at least one antibody in the serum that is indicative of *Trichinella spiralis* infection. As used herein, "under conditions that allow for selective binding" refers to reaction conditions, such as appropriate buffers, temperatures, and reaction times that enable selective binding of an antibody to an antigen that the antibody recognizes. Such conditions are known to those skilled in the art as are methods to optimize such conditions for a specific antigen-antibody interaction (see, for example, Sambrook et al., 1989, *Molecular Cloning: A Laboratory Manual*, Cold Spring Harbor Labs Press, Cold Spring Harbor, N.Y.; Su et al., *J. Parasitol.*, ibid.). Suitable assays can include, but are not limited to, solution assays as well as solution assays including a solid phase, and can be either competitive or non-competitive. That any such assay system is suitable for determining infection is due to the advantages of the diagnostic reagent per se: that the reagent is specific (i.e., can bind to anti-*Trichinella spiralis* antibodies with high affinity), selective, easy to prepare, and easy to use.

A preferred method to determine *Trichinella spiralis* infection in an animal includes the following steps: (a) applying serum collected from the animal onto a surface coated with a diagnostic reagent of the present invention under conditions such that selective binding of an antibody indicative of *Trichinella spiralis* infection to the reagent-coated surface is accomplished (i.e., occurs) in order to form a selective binding complex on the reagent-coated surface, (b) removing non-bound serum material under conditions that retain the selective binding complex on the reagent-coated surface, and (c) determining *Trichinella spiralis* infection by detecting the selective binding complex. As used herein, a "reagent-coated surface" is a surface to which a diagnostic reagent of the present invention is bound (i.e., adsorbed). As used herein, a "selective binding complex" refers to the complex formed when an antibody indicative of *Trichinella spiralis* infection binds to a diagnostic reagent of the present invention.

Suitable surfaces on which to coat a diagnostic reagent of the present invention include any surface to which a tyvelose-containing oligosaccharide and/or an effective carrier can bind in an essentially stable configuration (i.e., such that the oligosaccharide or carrier adsorbs to the surface and is not substantially removed from the surface during the assay). Preferably, a suitable plastic, glass, cell, or celluloid surface is used. In addition, the oligosaccharide and/or carrier should be able to bind to the surface without substantially interfering with the ability of the oligosaccharide to selectively bind to an antibody indicative of *Trichinella spiralis* infection. Examples of suitable surfaces include, but are not limited to, plate wells (e.g., in microtiter dishes), plates, dishes, tubes, beads, dip-sticks, filters (e.g., nylon, nitrocellulose, or derivatives thereof), and suitable celluloid-type matrices. Suitable assays to conduct using such surfaces include, but are not limited to, competitive or non-competitive ELISAs (enzyme-linked immunosorbent assays), Western blots, dot blots, radioimmunoassays, immunoprecipitation assays, agglutinin assays, Ouchterlony assays, and Mancini assays. Methods to coat antigens onto surfaces are well known in the art (see, for example, Carpenter, pp. 2–9, 1992, *The Manual of Clinical Laboratory Immunology*, 4th Edition, Rose et al., eds., American Society of Microbiology, Washington, D.C.; Su et al., *J. Parasitol.*, ibid.).

Conditions for removing non-bound serum material that retain the selective binding complex on the surface are known to those skilled in the art as are methods to optimize such conditions for a specific antigen-antibody complex (see, for example, Sambrook et al., ibid.; Su et al., *J. Parasitol.*, ibid.).

A number of methods known to those skilled in the art can be used to detect antigen-antibody binding interactions indicative of selective binding complexes of the present invention. For example, the actual binding reaction can be monitored by following changes in the configurations of the antigen and antibody, for instance by noting changes in electrical potential. The complex can also be identified using a compound, preferably labeled (i.e., an "identifying labeled compound"), which can selectively bind to the selective binding complex. Alternatively, an identifying compound, preferably labeled, that selectively binds to the antibody indicative of *Trichinella spiralis* infection while the antibody is attached to the diagnostic reagent can be used. Such a compound generally binds primarily to a non-binding epitope of the antibody. As used herein, a "non-binding epitope of the antibody" is a portion of the antibody that does not include the site at which the antibody binds selectively to the diagnostic reagent. Non-binding epitopes can include, for example, the constant regions of the antibody. Examples of compounds that can be used to detect selective binding complexes include secondary antibodies, such as antibodies that target antibodies of the species being tested (e.g., anti-pig antibodies in a pig assay); bacterial surface proteins that bind to antibodies, such as Protein A and Protein G; cells that interact with antibodies, such as T cells, B cells, and macrophages; eukaryotic cell surface proteins that bind to antibodies, such as Fc receptors; and complement proteins. Preferred compounds include secondary antibodies, Protein A and Protein G.

A variety of tags can be used to label compounds used to detect selective binding complexes of the present invention, including radioactive, enzymatic, or fluorescent labels. A preferred labeled compound of the present invention is an enzyme-linked compound capable of selectively binding to a non-binding site epitope of the antibody indicative of *Trichinella spiralis* infection. Depending on the label used, assays to determine *Trichinella spiralis* infection can be either qualitative or quantitative. Detection can be accomplished using a variety of well-known techniques, depending on the assay. For example, an enzymatic assay often yields a colorimetric product that can be detected visually or by a machine such as a densitometer or a spectrophotometer.

In a preferred embodiment, selective binding complexes are detected by a method including (a) contacting the selective binding complex with a labeled compound capable of binding selectively to the antibody indicative of infection or to the complex, (b) removing substantially all of the labeled compound that does not selectively bind to the complex, and (c) detecting the labeled compound, wherein presence of the labeled compound is indicative of *Trichinella spiralis* infection.

A particularly preferred assay system is an ELISA. In one embodiment, wells of a microtiter dish are coated with a diagnostic reagent of the present invention to form a reagent-coated surface. Effective coating can be accomplished by, for example, adding the diagnostic reagent, preferably contained in a buffer, to the wells and allowing the reagent-containing buffer to incubate in the wells at about 4° C. for several hours (e.g., overnight). The buffer is then removed and a blocking agent (e.g., milk or bovine serum albumin) is added to the reagent-coated wells in order to prevent non-selective and non-specific binding. The reagent-coated wells are washed, for example with phosphate buffered saline (PBS) containing small amounts of a detergent (e.g., about 0.05% Tween) to remove excess blocking agent. The serum to be tested for antibodies indicative of *Trichinella spiralis* infection is then added to the reagent-coated wells and incubated at about room temperature for about 1 hour to allow antibodies indicative of infection, if present in the serum, to bind to the reagent coating the wells (i.e., to form selective binding complexes). The wells are then washed using, for example, PBS containing Tween, to remove unbound serum material under conditions that retain the selective binding complexes attached to the wells. An enzyme-labeled secondary antibody conjugate (e.g., goat anti-pig IgG conjugated to horse radish peroxidase) is added to the wells and incubated under conditions to allow for binding between the secondary antibody and any selective binding complexes present in the wells. Excess secondary antibody is then removed (e.g., by washing with PBS containing Tween), enzyme substrate is added (e.g., 5'aminosalicyclic acid and hydrogen peroxide if the enzyme is horse radish peroxidase), and color change is monitored either visually or using, for example, a spectrophotometer or densitometer.

Another embodiment of the present invention is a diagnostic kit which includes at least one diagnostic reagent of the present invention. Suitable diagnostic reagents are heretofore disclosed. Preferably, the diagnostic reagent comprises a tyvelose-containing oligosaccharide conjugated to an effective carrier, such as a carrier heretofore disclosed. The kit can furthermore include a surface capable of being coated by the reagent. Preferably the surface is pre-coated by the reagent. Suitable surfaces are heretofore disclosed. A preferred surface is a dip-stick, particularly for field use. The kit can also include a means for detecting the binding of an antibody indicative of *Trichinella spiralis* infection (i.e., an indicative antibody) to the reagent. Suitable means for detection are heretofore disclosed. One example of a means (e.g., compound) to detect an indicative antibody is a secondary antibody that is raised against the constant regions of antibodies of the species being tested and that is conjugated to an enzyme that effects a color change in the presence of a suitable substrate.

In accordance with the present invention, anti-*Trichinella spiralis* drugs can be designed that are much safer and more effective than anthelminthic drugs currently available for use in treating trichinosis. Furthermore, apparently unlike current anthelminthic drugs, anti-*Trichinella spiralis* drugs of the present invention can be used for prophylaxis as well as treatment. Design of such drugs is based upon the discovery that tyvelose is found on *Trichinella spiralis* larvae and upon the assumption that the presence of tyvelose on *Trichinella spiralis* larvae and ES products is important physiologically to the parasite. In other words, if the parasite were unable to produce tyvelose, the parasite would die or fail to prosper.

Without being bound by theory, it is believed that tyvelose may play an important role in the physiology of the host-parasite relationship since the tyvelose-containing epitope is conserved among *Trichinella spiralis* isolates despite significant differences in nucleic acid sequences between isolates. Furthermore, it has been reported that ascarosides, which are composed of the 3,6-dideoxyhexose ascarylose joined to an alcohol, are important in maintaining the toughness and impermeability of Ascaris eggs to, for example, chemicals and in preventing eggs from desiccating (see, for example, Fairbairn et al., pp. 130–134, 1955, *Can. J. Biochem. Physiol.*, Vol. 33; Fairbairn, pp. 491–554, 1957, *Exp. Parasitol.*, Vol. 6).

Anti-*Trichinella spiralis* drugs of the present invention preferably inhibit the biosynthesis of tyvelose, preferably by being targeted against *Trichinella spiralis* enzymes that are essentially specific to tyvelose biosynthesis (i.e., enzymes involved in the biosynthesis of tyvelose but essentially not involved in the synthesis of compounds produced by mammals). Since mammals do not produce tyvelose and, thus, would be unlikely to produce proteins specific to tyvelose biosynthesis, it is believed that such drugs will be selectively targeted to *Trichinella spiralis* and, as such, will have substantially insignificant, if any, negative side effects.

Preferred anti-*Trichinella spiralis* drugs of the present invention can be produced in a variety of ways, including the following method: (a) enzymes that are essentially specific to tyvelose biosynthesis in *Trichinella spiralis* are identified; and (b) drugs are identified and/or synthesized that inhibit the activity of such enzymes, thereby inhibiting tyvelose production.

Several reports describe the pathways by which tyvelose and other 3,6-dideoxyhexoses are synthesized by, for example, Salmonella and *Yersinia pseudotuberculosis* (see, for example, Matsuhashi et al., pp. 4267–4274, 1966, *J. Biol. Chem.*, Vol. 241; Matsuhashi, pp. 4275–4282, 1966, *J. Biol. Chem.*, Vol. 241; Matsuhashi et al., pp. 4283–4287, 1966, *J. Biol. Chem.*, Vol. 241; Hey et al., pp. 5473–5478, 1966, *J. Biol. Chem.*, Vol. 241; and references included therein), and genes encoding at least these of enzymes have been isolated from Salmonella strains (see, for example, Wyk et al., pp. 5687–5693, 1989, *J. Bacteriol.*, Vol. 171; Verma et al., pp. 5694–5701, 1989, *J. Bacteriol.*, Vol. 171). Furthermore, ascarylose appears to be synthesized in a similar manner by Ascaris (Jezyk et al., pp. 707–719, 1967, *Comp. Biochem. Physiol.*, Vol. 23). Thus, at least some *Trichinella spiralis* enzymes specific to tyvelose synthesis may be identified, for example, by isolating enzymes similar to those used by bacteria and Ascaris to produce 3,6-dideoxyhexoses. Furthermore genes encoding *Trichinella spiralis* enzymes specific for tyvelose synthesis may be identified by homology with reported genes encoding certain steps of tyvelose synthesis in Salmonella serogroup D strains.

Once *Trichinella spiralis* enzymes essentially specific to tyvelose biosynthesis have been identified, potential drugs can be identified and produced that inhibit tyvelose biosynthesis, for example, by a screening program of organic molecules to identify those that specifically inhibit activity of the enzyme or by rational drug design in which, for example, the active site of the enzyme is identified and a drug designed that would interfere with the active site.

Anti-*Trichinella spiralis* drugs of the present invention can be administered to animals in effective amounts in order to protect animals from trichinosis. Effective amounts and dosing regimens can be determined using techniques known to those skilled in the art. It is also within the scope of the present invention that anti *Trichinella spiralis* drugs of the present invention can also be used to treat infection by any organism, including any Trichinella parasite, having tyvelose-containing antigenic epitopes.

The following examples are provided for the purposes of illustration and are not intended to limit the scope of the invention.

EXAMPLES

Example 1. Carbohydrate analysis of *Trichinella spiralis* muscle stage larval antigens This example describes the identification of monosaccharide compositions of *Trichinella spiralis* muscle larval antigens, including TSL-1 antigens, $L_1$ larval homogenates, and $L_1$ ES (excretory/secretory) products.

*Trichinella spiralis* $L_1$ larval homogenates, TSL-1 antigens (i.e., Tsp 130 immunoaffinity-purified group II antigens), preparations enriched for a 43 kDa TSL-1 antigen, and ES antigens were prepared as described in Denkers et al., *J. Immunol.*, ibid., and Denkers et al., *Mol. Biochem. Parasitol.*, ibid.

Total monosaccharide compositions of the larval homogenate, TSL-1 antigens, and ES antigens were determined by gas chromatography/mass spectrometry (GC/MS) of both the trimethylsilyl (TMS) ethers of methyl glycosides and of the alditol acetate derivatives of the glycosyl residues. TMS methyl glycosides were prepared by acidic methanolysis, re-N-acetylation, and trimethylsilylation. The general procedure for analysis of carbohydrate components of glycoproteins described by Chaplin, pp. 336–341, 1982, *Anal. Biochem.*, Vol. 123, was used, with the following modifications: (a) scyllo-inositol (2 nanomoles) was used as the internal standard; (b) samples were dried (e.g., in a Speed-Vac Concentrator SVC100H, available from Savant Instruments Inc., Farmingdale, N.Y. in 1.0 milliliter (ml) Reacti-Vials (available from Pierce, Rockford, Ill.); (c) acidic methanolysis was conducted by adding 40 microliters (μl) of 3M methanolic HCl (available from Supelco, Bellefonte, Pa.) and 10 μl methyl acetate (available from Aldrich, Milwaukee, Wis.), sealing the vial with a teflon-lined septa in an open-top screw cap (available from Pierce), vortexing, and heating to about 70° C. for about 4 hours; (d) trimethylsilylation was achieved by adding 20 μl Sylon HTP (available from Supelco), vortexing, and heating to about 70° C. for about 20 minutes.

Dry derivatized samples were dissolved in HPLC-grade hexanes and the insoluble salts were allowed to settle. A portion of the clear hexane-extracted sample was analyzed by GC/MS on a gas chromatograph connected to a mass selective detector (e.g., Hewlett-Packard (HP) 5980 gas chromatograph and HP 5970 mass selective detector, each available from Hewlett-Packard, Palo Alto, Calif.). Samples were injected in the spitless mode, using, for example an HP 12-m HP-1 column and dry oxygen-free helium as the carrier gas. The oven was programmed to hold at about 80° C. for about 1 minute followed by an about 30° C. per minute rise to about 100° C., an about 10° C. per minute rise to about 265° C., an about 5 minute hold at about 265° C., and a final about 2 minute hold at about 280° C. The mass spectrometer was set to scan from mass to charge ratio (m/z) about 50 to about 800 atomic mass units (amu) at about 0.81 scans/second. TMS-derivatives were identified by both characteristic retention times and mass spectra electron impact fragmentation patterns compared to those of authentic standards. Quantitation was achieved by integration of specific ion peak areas (m/z 204—pentoses and hexoses; m/z 173—hexosamines; m/z 318—inositols) with response factors calculated from known concentrations of standards prepared under identical conditions as the samples. Standards included: xylose, rhamnose, fucose, mannose, galactose, glucose, scyllo-inositol, myo-inositol, N-acetylgalactosamine (galNAc), N-acetylglucosamine (glcNAc), N-acetylneuraminic acid, *Salmonella typhimurium* lipopolysaccharide (LPS), *Salmonella enteritidis* LPS, and *Escherichia coli* LPS serotype O55:B5, all of which are available from Sigma Chemical Co., St. Louis, Mo.; chemically synthesized methyl tyvelose, methyl abequose, and methyl paratose were obtained from Dr. D. R. Bundle, Division of Biological Sciences, National Research Council of Canada, Ottawa, Ontario, Canada; and *Ascaris suum* eggs containing ascarylose were obtained from infected pigs.

Alditol acetate derivatives were prepared by trifluoroacetic acid (available from Pierce) hydrolysis of the antigen samples, followed by sodium borohydride or borodeuteride (each available from Sigma) reduction and acetylation. The general procedure for formation of the alditol acetate derivatives described in York et al., pp. 3–40, 1986, *Methods Enzymol.*, Vol. 118, as modified by Waeghe et al., pp. 281–304, 1983, *Carbohyd. Res.*, Vol. 123, for analysis of small amounts of samples, was used. Further modifications included: (a) scyllo-inositol (2 nanomoles) as the internal standard; (b) O-acetylation of the alditols by addition of 100 µl acetic anhydride (available from Supelco) and heating to about 121° C. for about 1 hour; and (c) partitioning of the per-O-acetylated alditols between about 1 ml chloroform and about 1 ml water. Dry samples were dissolved in acetone, and a portion was applied to the GC/MS as above. The oven was programmed to hold at about 50° C. for about 1 minutes, followed by an about 30° C. per minute rise to about 165° C. and an about 10° C. per minute rise to about 280° C., with a final about 2 minute hold at about 280° C. The mass spectrometer was set to scan from m/z about 80 to about 450 amu at about 1.48 scans/second.

A 3,6-dideoxyhexose, which was not seen as the TMS-methyl glycoside, was identified by alditol acetate derivation. To quantitate this sugar, equal amounts of fucose and chemically synthesized methyl tyvelose were subjected to alditol acetate derivatization, and the peak area ratio was calculated. This response factor was used to quantitate the amount of 3,6-dideoxyhexose in the *Trichinella spiralis* samples based on the amount of fucose in both the trimethylsilyl and alditol acetate preparations.

The glycosyl compositions of the Tsp 130 immunoaffinity-purified TSL-1 antigen, ES antigens and muscle stage larval homogenate are shown in Table 1.

TABLE 1

Glycosyl compositions of *Trichinella spiralis* muscle stage larval antigens

| | TSL-1 antigens[a] | ES antigens[a] | Larval homogenate[a] |
|---|---|---|---|
| tyvelose[b] | 24 | 21 | 8 |
| fucose | 36 | 19 | 12 |
| xylose | 0 | 1 | 1 |
| mannose | 22 | 17 | 19 |
| galactose | 0.5 | 2 | 2 |
| glucose | 1 | 4 | 19 |
| galNAc | 9 | 15 | 13 |
| glcNAc | 7 | 21 | 25 |
| myo-inositol | 0.5 | 0 | 1 |
| sialic acid | 0 | 0 | 0 |

[a]mean of 4 values obtained from 2 separate GC/MS analyses on each of 2 different antigen preparations of TSL-1 antigens, ES antigens, and larval homogenate. Values are molar percentages of total glycosyl residues found.
[b]3,6-dideoxy-D-arabinohexose All sugars listed, with the exception of the 3,6-dideoxyhexose, were identified by retention time and mass spectra following methanolysis, re-N-acetylation, and trimethylsilylation, and quantitated based on peak area. The 3,6-dideoxyhexose was detected only as the alditol acetate derivative. It was not found as the trimethylsilyl derivatized methyl glycoside, nor as any other TMS derivative (i.e., trimethylsilyl butyl glycoside).

The glycosyl composition of the TSL-1 fraction was surprising in two respects: (a) fucose accounted for about 36 molar percent of the total glycosyl residues; and (b) a 3,6-dideoxyhexose was identified, which accounted for at least about 24 molar percent of the glycosyl residues. The 3,6-dideoxyhexose also was found in preparations greatly enriched for the 43-kDA TSL-1 glycoprotein antigen. Similar to the TSL-1 antigens, the glycosyl composition of the ES antigens was shown to have large amounts of fucose (about 19%) and 3,6-dideoxyhexose (about 21%). In addition, the ES antigens were comprised largely of hexosamines (about 15% N-acetylgalactosamine and about 21% N-acetylglucosamine). The crude larval homogenate also had relatively high amounts of fucose (about 12%) and hexosamines (about 13% N-acetylgalactosamine and about 25% N-acetylglucosamine), while the 3,6-dideoxyhexose was found in lower amounts (about 8%) compared to the TSL-1 and ES antigens.

Example 2. Determination of the 3,6-dideoxyhexose relative configuration

This example indicates that the *Trichinella spiralis* 3,6-dideoxyhexose identified in Example 1 is 3,6-dideoxyarabinohexose.

Identification of the *Trichinella spiralis* 3,6-dideoxyhexose relative configuration was achieved by comparing GC retention times of various per-O-acetylated bacterial and parasitic 3,6-dideoxyhexoses after conversion to alditol acetate derivatives. Chemically synthesized standards included methyl tyvelose (3,6-dideoxy-D-arabinohexose), methyl abequose (3,6-dideoxy-D-xylohexose), and methyl paratose (3,6-dideoxy-D-ribohexose). In addition, acid hydrolysates of biological materials containing 3,6-dideoxyhexoses were used, including colitose (3,6-dideoxy-L-xylohexose) released from *Escherichia coli* LPS, abequose (3,6-dideoxy-D-xylohexose) released from *Salmonella typhimurium* LPS, tyvelose (3,6-dideoxy-D-arabinohexose) released from *Salmonella enteritidis* LPS, and ascarylose (3,6-dideoxy-L-arabinohexose) released from decoated *Ascaris suum* eggs. The identification of relative configuration was verified by co-injection with authentic standards.

The alditol acetate derivative of the TSL-1 and ES 3,6-dideoxyhexose showed the same chromatographic mobility and mass spectrum as the alditol acetate derivatives of standards containing 3,6-dideoxyarabinohexose. On the non-chiral GC column, D- and L- alditol acetate enantiomers necessarily co-elute. In contrast, the alditol acetate derivatives prepared from chemically synthesized methyl paratose, chemically synthesized methyl abequose, from abequose released from *Salmonella typhimurium*, and from colitose released from *Escherichia coli* all had identical mass spectra but were chromatographically distinguishable. Both the ribo and xylo 3,6-dideoxyhexose derivatives eluted later than the arabino 3,6-dideoxyhexose derivatives, suggesting that the TSL-1 3,6-dideoxyhexose was of the arabino configuration.

Example 3. Determination of the 3,6-dideoxyhexose absolute configuration

This example indicates that the *Trichinella spiralis* 3,6-dideoxyhexose identified in Example 1 is 3,6-dideoxy-D-arabinohexose (i.e., tyvelose).

Assignment of the absolute configuration of the TSL-1 and ES 3,6-dideoxyhexose was achieved by GC/MS analysis of the acetylated glycosides formed from chiral 2-octanol. 3M HCl in both (−)-2 and (+)-2 octanol (available from Sigma) were prepared by the dropwise addition of about 256 µl acetyl chloride (available from Mallinkrodt, Inc., Paris, Ken.) to about 1.2 ml octanol. Derivatizations of TSL- 1 and ES antigens were achieved by: (a) hydrolysis in 2M TFA at about 121° C. for about 1 hour (hr); (b) octanolysis in either (−)-2 or (+)-2 3M octanol HCl at about 80° C. for about 3 hr; (c) addition of sodium acetate; and (d) acetylation in acetic anhydride at about 100° C. for about 1 hr. The acetylated octyl glycosides were partitioned into the organic phase between about 1 ml chloroform and about 1 ml water, dried, and extracted into acetone (see, for example, Leontein et al., pp. 359–362, 1978, *Carbohyd. Res.*, Vol. 62). Samples were analyzed by GC/MS as above for alditol acetates (total ion chromatogram) or in the selected ion monitoring mode (selecting m/z's of about 83, 85, 112, 145, and 215). Methyl tyvelose (3,6-dideoxy-D-arabinohexose) and *Ascaris suum* eggs (containing 3,6-dideoxy-L-arabinohexose) were also subjected to hydrolysis, (−)-2 and (+)-2 octanolysis, and acetylation. GC/MS data from the resulting acetylated 3,6-dideoxyarabinohexose octyl glycoside derivatives were compared to those obtained from the TSL-1 and ES antigen samples. Verification of absolute configuration was achieved by co-injection.

The absolute configuration of the *Trichinella spiralis* 3,6-dideoxyarabinohexose was identified as D- on the basis of retention time and mass spectra of the acetylated, optically pure, 2-octyl glycosides. Both the acetylated (−)-2 and (+)-2 octyl glycosides of TSL-1 3,6-dideoxyarabinohexose from TSL-1 and ES co-eluted with the corresponding acetylated (−)-2 and (+)-2 octyl glycosides derived from chemically synthesized tyvelose (3,6-dideoxy-D-arabinohexose). Correspondingly, as required, the acetylated (−)-2 and (+)-2 octyl glycosides of TSL-1 3,6-dideoxyarabinohexose co-eluted with their respective enantiomers, namely the acetylated (+)-2 and (−)-2 octyl glycoside derivatives of ascarylose (3,6-dideoxy-L-arabinohexose) derived from *Ascaris suum* eggs. Therefore, the *Trichinella spiralis* sugar was designated as 3,6-dideoxy-D-arabinohexose (tyvelose) on the basis of the determination of relative configuration by alditol acetate derivatization and of the determination of absolute configuration by acetylation of the chiral octyl glycosides.

Example 4. Methylation analysis

This example demonstrates determination of the glycosyl composition of TSL-1 carbohydrates.

TSL-1 antigens (670 μg protein) were buffer exchanged from PBS/NaN$_3$ into 18 megaohm Milli-Q (available from Millipore Corp., Bedford Mass.) by centrifugation at 5000 × g in a BSA-passivated Centriprep C-10 (available from Amicon, Danvers, Mass.). The carbohydrates were then treated with about 100 μl 1M NaBD$_4$ in 50 mM NaOH at about 45° C. for about 20 hr to β-eliminate and reduce O-glycosidically-linked oligosaccharides. Following addition of glacial acetic acid and evaporation, the sample was redissolved and evaporated in 10% acetic acid in methanol (about 3 times) and in absolute methanol (about 3 times). The sample was then desalted by cation exchange column chromatography (330 μl BioRad (Hercules, Calif.) AG50W-X 8 resin, H+ form, 1.7 meq/ml, packed on a 5 mm silanized glass wool plug in a 5¾ inch silanized Pasteur pipet). The carbohydrates were eluted with Milli-Q water until the pH of the eluate became neutral. The eluate was concentrated to about 0.5 ml, transferred to a 1.0 ml Reacti-Vial, and dried to completion. TSL-1 carbohydrate antigens were methylated by the Hakomori procedure (see, Hakomori, pp. 205–208, 1964, *J. Biochem.* (Tokyo), Vol. 55), as adapted by Sandford and Conrad (see, Sandford et al., pp. 1508–1517, 1966, *Biochem.*, Vol. 5) and as modified for microanalysis by Waeghe et al., ibid. The sample was initially dissolved in about 250 μl dry dimethylsulfoxide (available from Pierce), with continuous stirring for about 2 hr at room temperature. About 20 μl of 4.5M sodium dimethylsulfinyl carbanion (see, for example, York et al., ibid.; Stellner et al., pp. 464–472, 1973, *Arch. Biochem. Biophys.*, Vol. 155) was added, and the reaction mixture was stirred for about 2 hr at room temperature. About 35 μl of methyl iodide (available from Aldrich) was added dropwise, and the mixture was stirred for 12 hr at room temperature. The reaction mixture was diluted with water to obtain a 1:1 (v:v) dimethyl sulfoxide:water solution, and the pre-reduced, per-O-methylated carbohydrates were recovered and purified by reverse-phase chromatography on a Sep-Pak C-18 cartridge (available from Waters Associates, Inc., Milford, Mass.) (see Waeghe et al., ibid.). The final two elution fractions (2 ml 100% acetonitrile for per-O-methylated alditols d.p. 2–10; 4 ml 100% EtOH for per-O-methylated alditols of larger oligosaccharides d.p.>10 and polysaccharides) were collected in 13×100 mm test tubes and the solvent was evaporated to dryness using a stream of filtered air at room temperature. The per-O-methylated carbohydrates were converted into their partially O-acetylated, partially O-methylated alditols by hydrolysis in 2M TFA, reduction with NaBD$_4$, and acetylation with acetic anhydride (York et al., ibid.). Glycosyl linkage composition was determined by GC/MS of the partially O-acetylated, partially O-methylated alditols using the temperature program as described for alditol acetates. The hexosamine residues were identified by comparing retention times and mass spectra to undermethylated N-acetylglucosamine and N-acetylgalactosamine standards. Verification of these designations was achieved by co-injection.

Results from the characterization of TSL-1 glycosyl linkages as determined by Hakomori methylation of the TSL-1 antigens are shown in Table 2.

TABLE 2

| Glycosyl linkage composition of TSL-1 carbohydrates | |
| --- | --- |
| Sugar | Mole percent |
| t-tyvelose[a,b] | 8.8 |
| t-fucose[b] | 13.8 |
| t-mannose | 1.9 |
| 3,4-fucose | 2.7 |
| 2-mannose | 3.9 |
| 2,4-mannose | 7.6 |
| 2,6-mannose | 5.5 |
| 3,6-mannose | 10.1 |
| 4-glcNAc[c] | 9.7 |
| 3-galNAc[c] | 14.5 |
| 3,4-glcNAc[c] | 21.4 |

[a] 3,6-dideoxy-D-arabinohexose
[b] the yields of t-tyvelose and t-fucose were lower than would be expected, presumably due to their acid-liability and/or volatility
[c] hexosamines identified by comparing retention times and mass spectra to undermethylated N-acetylglucosamine and N-acetylgalactosamine standards The TSL-1 3,6-dideoxy-D-arabinohexose was found to be present entirely as non-reducing terminal residues. Approximately 83% of the fucose was also present as non-reducing terminal residues, with the remaining fucose found as 3,4-linked branched residues. The mannosyl derivatives found included terminal, 2-linked, 2,4-linked, 2,6-linked, and 3,6-linked residues. Because the entire TSL-1 sample was methylated without first separating N- and O-linked sugars, it is probable that these residues may be constituents of both N-linked and O-linked glycoproteins.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A diagnostic reagent to detect Trichinella infection comprising tyvelose joined through glycosidic linkage to at least one monosaccharide to form a disaccharide or an oligosaccharide, said reagent comprising at least one tyvelose terminal residue said tyvelose being joined to a monosaccharide other than mannose, said reagent being capable of selectively binding to an antibody indicative of said infection.

2. The reagent of claim 1, wherein said reagent is capable of detecting *Trichinella spiralis* infection.

3. The reagent of claim 1, wherein said tyvelose-containing reagent is conjugated to a carrier.

4. The reagent of claim 1, wherein said monosaccharide is selected from the group consisting of tyvelose, fucose, N-acetylgalactosamine and N-acetylglucosamine.

5. The reagent of claim 1, wherein said tyvelose-containing reagent comprises a disaccharide.

* * * * *